United States Patent
Aoyagi et al.

(10) Patent No.: US 6,230,035 B1
(45) Date of Patent: May 8, 2001

(54) APPARATUS FOR DETERMINING CONCENTRATIONS OF LIGHT-ABSORBING MATERIALS IN LIVING TISSUE

(75) Inventors: Takuo Aoyagi; Masayoshi Fuse; Chen-tai Xie; Michio Kanemoto, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/356,521

(22) Filed: Jul. 19, 1999

(30) Foreign Application Priority Data

Jul. 17, 1998 (JP) .................................................. 10-203388
Mar. 11, 1999 (JP) .................................................. 11-065489

(51) Int. Cl.⁷ ........................................................ A61B 5/00
(52) U.S. Cl. ........................................... 600/336; 600/310
(58) Field of Search ................................... 600/310, 322, 600/323, 336

(56) References Cited

U.S. PATENT DOCUMENTS 5,385,143 * 1/1995 Aoyagi ................................. 600/310
5,596,987 * 1/1997 Chance ................................. 600/310

FOREIGN PATENT DOCUMENTS 53-26437 8/1978 (JP) .

OTHER PUBLICATIONS

Shibata, Kazuo, *Spectrophotometry of Translucent Biological Materials—Opal Glass Transmission Method*, Methods of Biochemical Analysis, vol. VII, New York, 1959, pp. 77–109.

* cited by examiner

Primary Examiner—Eric F. Winakur
(74) Attorney, Agent, or Firm—Sughrue, Mion, Zinn, Macpeak & Seas, PLLC

(57) ABSTRACT

Irradiating device 3 of a pulse oximeter includes a scattering plate 6. Scattering light is projected into a living tissue. The diameter of the incident area is sufficiently large compared with that of a light receiving area or vice versa. Therefore, tissue terms in a theoretical formula of Φ which represents a ratio of changes of optical densities of tissue measured with two wavelengths are not dependent on the wavelength. The digital processor 10 calculates an oxygen saturation by substituting Φ measured into simultaneous equations.

8 Claims, 9 Drawing Sheets

APPARATUS FOR DETERMINING CONCENTRATIONS OF LIGHT-ABSORBING MATERIALS IN LIVING TISSUE

BACKGROUND OF THE INVENTION

1. Field of the Invention

The present invention relates to an apparatus for determining concentrations of light absorbing materials in a living tissue by the utilization of intensities of light transmitted through or light reflected from the living tissue.

2. Related Art

A pulse oximetry is known as one of this type of instrument. The pulse oximetry noninvasively measures an oxygen saturation in arterial blood by the utilization of pulsations of light transmitted through a living tissue. To this end, the oximetry irradiates a living tissue with light of two wavelengths to produce pulsations of light L1 and L2; obtains changes $\Delta A1$ and $\Delta A2$ of the optical densities of the living tissue by the utilization of the pulsations of light; and computes an arterial oxygen saturation $SaO_2$. Before computing the $SaO_2$ from the $\Delta A1$ and $\Delta A2$, $\Phi 12 = \Delta A1/\Delta A2$ must be computed. Conversion of $\Phi 12$ into $SaO_2$ is carried out by use of a relationship between $\Phi 12$ and $SaO_2$ of a human body, which are actually measured. The principle of this method is applicable to the measurement of every kind of light absorbing material contained in arterial blood. This method, called a pulse photometry, is practically used for the measurement of a dye dilution curve.

A near-infrared spectrometry (NIRS) is also known as another example of this type of measuring technique. The NIRS noninvasively measures an average oxygen saturation in arterial blood and venous blood by use of a light transmitted through the living tissue. This measuring technique is also applied to the method of measuring light absorbing materials in any of the other tissues than the blood. Example of those light absorbing materials are cytochrome and myoglobin. The near-infrared spectrometry produces an intended value from a received light by substituting measured intensities of light of wavelengths for a theoretical formula of light scattering Various theoretical formulae have been proposed.

Errors inevitably occur in noninvasively measuring a ratio of concentrations of light absorbing materials in a living tissue or in blood. Many causes for the error are known. In the case of the pulse oximetry, there exist many light absorbing materials and the pulsation of the living tissue exists as well as $SaO_2$ as an object to be measured, those factors will cause errors in the $SaO_2$ measurement.

Where an attempt is made to remove the adverse effects by those factors and to improve a measurement accuracy, the necessity is to increase the number of wavelengths of light used and the number of the related formulae, and to arrange those formulae into simultaneous equations and to solve the resultant.

The blood as one of the key light absorbing materials as well as the tissue, exhibits a nature of light scattering. Many factors are involved in the optical measurement of scattering material. Light tends to scatter in a short wavelength region. Then, when incident and collimated light rays propagate through the tissue, scattering of light gradually grows and the propagating paths of light are different with their wavelengths This fact is essential to secure an improved accuracy of measurement, and requires complicated numerical correction.

A variety of methods have been used for the near-infrared spectrometry (NIRS), but reliable methods have never been presented so far as we know. This fact shows an intricacy of the problem by the scattering nature.

SUMMARY OF THE INVENTION

For the above background reasons, the present invention provides an inventive and creative approach to an optical measuring system which enables a measuring system of light scattering material to be described by theoretical expressions, whereby simple calculations and an improved measuring accuracy are both realized.

A first aspect of the invention provides an apparatus which irradiates a living tissue with light of different wavelengths, receives light transmitted through or light reflected from the living tissue, converts the light into a corresponding electrical signal, and computes a ratio of concentrations of light absorbing materials in the living tissue, the apparatus comprising: irradiating means being arranged such that a scattering level of the irradiating light on the tissue is sufficiently large, and concentration-ratio computing means for computing a ratio of concentrations of light absorbing materials on the assumption that non-absorptive attenuations are equal independently of the wavelengths of light Preferably, the concentration-ratio computing means computes a ratio of concentrations of light absorbing materials by a theoretical formula where the terms of tissue exculsive of the blood about respective wavelengths are equal.

Alternatively, the. concentration-ratio computing means computes changes of optical densities of the living tissue by use of pulsations of intensities of transmitted light, and computes a ratio of concentrations of light absorbing materials by use of the computed changes of the optical densities.

Preferably, the concentration-ratio computing means comprises: optical density-change calculating means for calculating optical density changes $\Delta A1$ to $\Delta A2$, ... $\Delta An$ of an n number of wavelengths from the pulsations of light transmitted through or light reflected from the living tissue, which is irradiated with the irradiating means; optical density change-ratio calculating means for calculating a ratio $\Phi ij$ of two optical density changes ($\Delta Ai$, $\Delta Aj$) of each of an n−1 number of combinations each consisting of two optical density changes ($\Delta Ai$, $\Delta Aj$), which are preselected from among the n number of optical density changes $\Delta A1$ to $\Delta An$ calculated by the optical density-change calculating means; computing means for computing an arterial oxygen saturation or a ratio of concentrations of another in-blood light absorbing material by use of the n−1 number of $\Phi ij$ obtained by the optical density change-ratio calculating means and an n−1 number of simultaneous equations constructed such that the terms of tissue exclusive of the blood about respective wavelengths are equal on the assumption that the optical density change is equal to a difference between an optical density change of blood and that of tissue exclusive of the blood.

In the present invention, the irradiating means includes a scattering plate and a light source for irradiating a living tissue with light through the scattering plate.

In the present invention, the irradiating means includes a reflecting plate with a reflecting surface, a scattering plate and a light source :or irradiating a living tissue with light with the aid of the reflecting plate and the scattering plate.

In the present invention, an area for receiving light transmitted through or light reflected from the living tissue is selected to be sufficiently large or small with relation to an irradiation area on the living tissue.

Specifically, a ratio of the irradiating area on the living tissue to an effective area of the light receiving area on the living tissue is 1:2 or more or 2 or more: 1.

Preferably, the light scattering plate is a white acrylic plate.

DETAILED DESCRIPTION OF PREFERRED EMBODIMENTS

Principles of Present Invention

Figure 1:
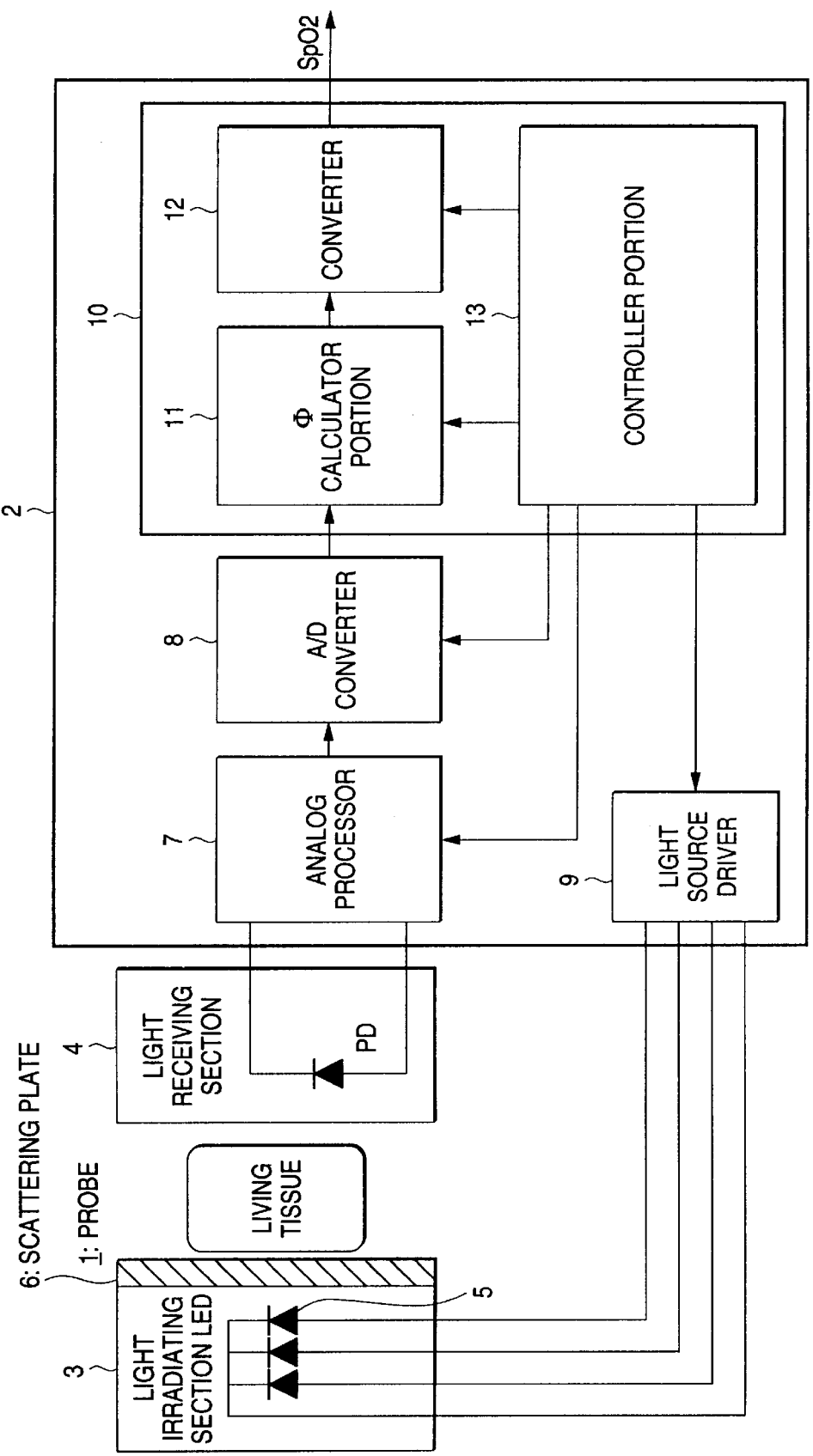
FIG. 1 is a an overall arrangement of the pulse oximeter constructed according to the present invention.

The principles of the invention will be described. The sky, which does not contain light absorbing materials, looks bluish or reddish in some conditions. This phenomenon arises from the fact that fine particles extremely thinly present in the air cause wavelength-dependent scattering of light. A cloud looks white. The reason for this is that fine particles not absorbing light are densely present in the air, and multiple scattering of light occurs, and as a result, the scattering loses its wavelength-dependency. The fact that the scattering has no wavelength dependency is very convenient for the measuring of light absorbing materials in a scattering material. For this reason, the present invention is based on the irradiation of a living tissue as an object to be measured with scattering light.

A. Schuster theoretically described a field of multiple scattering of light. Schuster's theory will be described briefly. (For detail of the theory, reference is made to "Radiation through a Foggy Atmosphere", written by A. Schuster, Astrophysical Journal 21(1), 1–22 (1905).)

In the Schuster's theory, there is no wavelength dependency of the scattering because the incident light is sufficiently scattered and uniformly incident on a sufficiently large area of the object.

Under the conditions, Schuster set up the following formula:

$$Iin/Iout = Pexp(QD) - (P-1)exp(-QD)$$

where $Q = \{K(K+2B)\}^{1/2}$, and $P = (1+a)^2/4a$, and $a = \{K/(K+2B)\}^{1/2}$.

In the above formula, Iin is an incident light intensity; Iout is a transmitted light intensity; K is an absorption coefficient; and B is a scattering coefficient.

If light absorption is sufficiently large, and QD is sufficiently large, Iin/Iout=Pexp(OD), and hence A (optical density)=ln(Iin/Iout)=lnP+PD. The NIRS (near-infrared spectrometry) is based on this equation. In the case of the pulse photometry, when a thickness D of an object changes by a quantity of ΔD, an extinction-level change ΔA is given by $$\Delta A = Q \times \Delta D = \{K(K+2B)\}^{1/2} \times \Delta D$$

Thus, only the absorption coefficient depends on the wavelength in both the relation of the optical density to the light absorbency and the relation of the optical density change to the light absorbency. The absorption coefficient may take a known value, and this is convenient in practical use.

If no absorption is present, Iin/Iont=1+BD, and thence the optical density A=ln(Iin/Iout)=ln(1+BD). When a thickness D of a object changes by a quantity of ΔD, an optical density change ΔA is given by $$\Delta A = \Delta ln(Iin/Iout) = ln\{(1+B(D+\Delta D))\} - ln(1+BD) = ln[\{(1+B(D+\Delta D))\}/(1+BD)] = ln[1+B\Delta D/(1+BD)]$$

If the thickness D is sufficiently large, ΔA=ln1=0. Thus, an optical density vs. wavelength characteristic curve is not dependant on the wavelength when no absorption is present.

A measuring system for measuring light absorbing materials in an object by use of Schuster's theory must satisfy the following conditions:

1) The non-absorptive attenuation has no wavelength dependency.
2) A relation of the optical density to the absorption coefficient satisfies the above theoretical formula.

Let us consider the condition 1). When parallel light beams are incident on a scattering object, scattering of light increases as light propagates through the object In other words, light must pass through an object having a thickness to transform the parallel light into light sufficiently scattered. An optical path when light passes through the object is dependent on the wavelength. Therefore, to completely remove the wavelength dependency of the scattering, it is necessary to sufficiently increase a degree of scattering of the incident light on the surface of the object.

An empirical methodology for proving the validity of the condition satisfying method to satisfy the condition 1) will be described.

Figure 10:
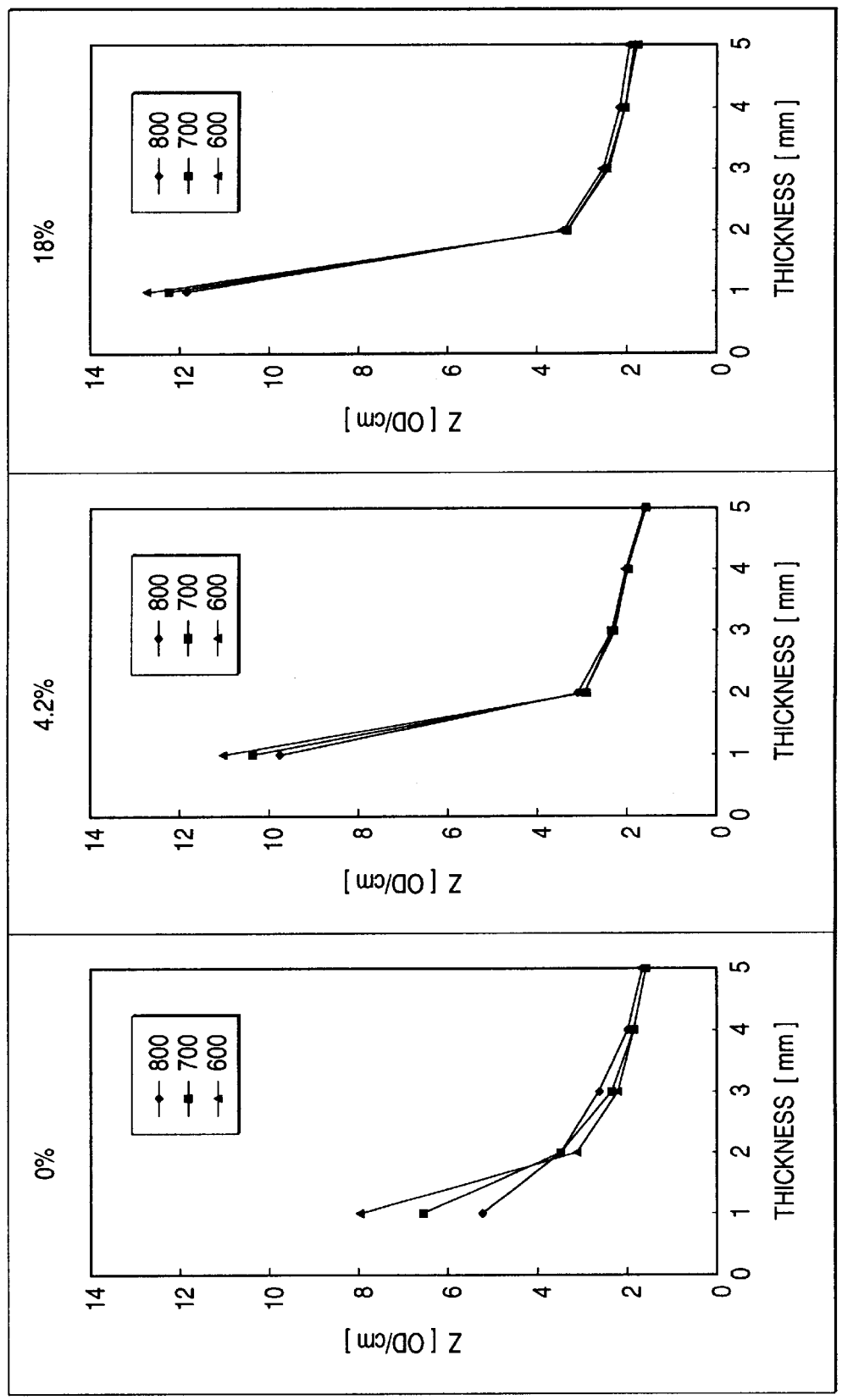
FIG. 10 is a graph showing the results of another measurement.

In a measuring apparatus used, an integral sphere was assembled into a spectro-photometer. Cells containing milk of 1 mm, 2 mm, 3 mm, 4 mm and 5 mm thick were used for object. Each cell was 6 mm in height and width. An optical density increment ΔA was measured every 1 m (ΔD) of a milk thickness increment,and an optical attenuation coefficient Z (=ΔA/ΔD) was calculated. values of the optical attenuation coefficient Z were plotted as shown in FIG. 10. As seen from the graphs of FIG. 10, as the thickness of the object increases and a degree of scattering increases, the optical attenuation coefficient z decreases and its wavelength-dependency decreases. Three types of milk were used; first milk containing 0% fat, second milk containing 4.2% fat and third milk containing 18% fat. The wavelengths of light for measurement were 600 nm, 700 nm and 800 nm. Those wavelengths are selected for the reason that an absorption of light by the fat content is large in wavelengths shorter than the selected ones, and the light absorption by water is large in wavelengths longer than the selected ones.

Let us consider the condition 2) above. In the absorptive attenuation, the length of the optical path in the light absorbing material increases by scattering$_1$ so that the optical absorption increases in amount. As seen from the formula, a changing rate of the absorption increase becomes small as the absorption coefficient becomes large if the scattering coefficient is fixed. In this case, the relationship between the optical absorption and the optical attenuation shows a curve. If no scattering is present, B=0. In this case, the optical path is not increased, the optical attenuation is equal to the optical absorption. As the scattering increases, the optical path increases, the gradient becomes large, and the relationship between the optical absorption and the optical attenuation asymptotically approaches to a curve at a limiting point. This limit is expressed by the absorptive attenuation theoretical formula described above. At the limit, the optical attenuation value one-to-one corresponds continuously to absorption value. The conventional measuring system cannot satisfy the two conditions 1) and 2) above, and hence its measuring accuracy based on Schuster's theorem is poor.

A first way to satisfy the condition 2) is to satisfy the incident light condition and to set an irradiation area on the living tissue to be sufficiently larger than a light receiving area on the same tissue. If so done, the transmitted light uniformly distributed on the transmit side of the object can be measured. Therefore, Schuster's theorem is satisfied and the measurement result is correct.

Figure 5:
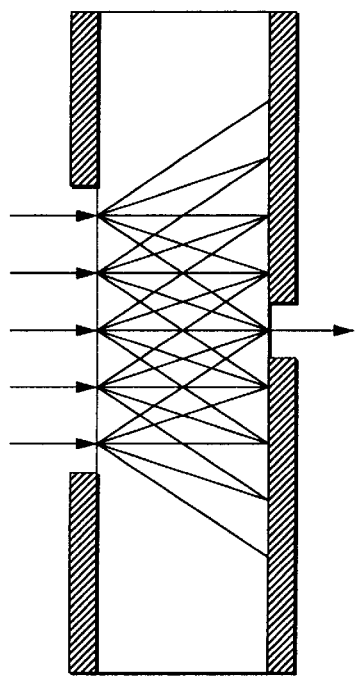
FIGS. 5(a)–5(b) are diagrams showing the relationship between an incident window and a transmission window.
Figure 5:
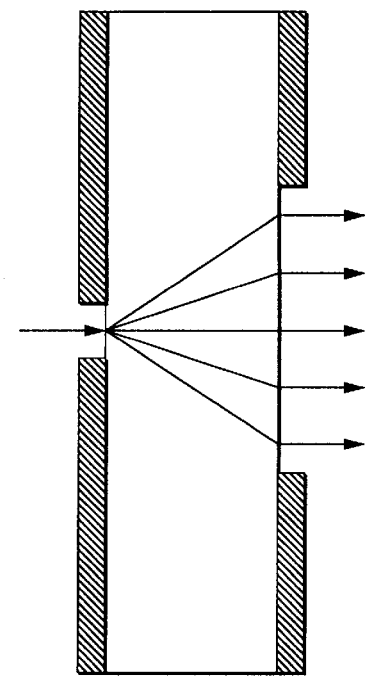

A second way to satisfy the condition 2) is to set the light receiving area on the living tissue to be sufficiently larger than the irradiation area. The reason for this will be described with the aid of a model diagram of FIGS. 5a and 5b. In each model of FIGS. 5a and 5b, an incident window and an transmission window are set on an object to be measured. Light is incident onto the incident window, transmitted through the object, and exits through the transmission window. Optical paths of light within the object are representatively depicted. In the case of FIG. 5a, the diameter of the incident window is much larger than that of the transmission window. In the case of FIG. 5b, the diameter of the transmission window is much larger than that of the incident window. In the FIG. 5a case, rays of incident light spread during the course of its traveling within the object under measurement. The light is gathered from every part of the light, and received. In the FIG. 5b case, rays of incident light spread during the course of its traveling within the object under measurement. All the light rays are received. The optical paths of light rays received in the FIG. 5b case are opposite in direction to those received in the FIG. 5a; however, the configuration of the former case is the same as of the latter case. Therefore, the measurement result yielded in the FIG. 5b case is the same as in the FIG. 5a case. In practical use, the FIG. 5b case is superior to the FIG. 5a case since the former needs smaller optical energy compared with the latter.

Figure 6:
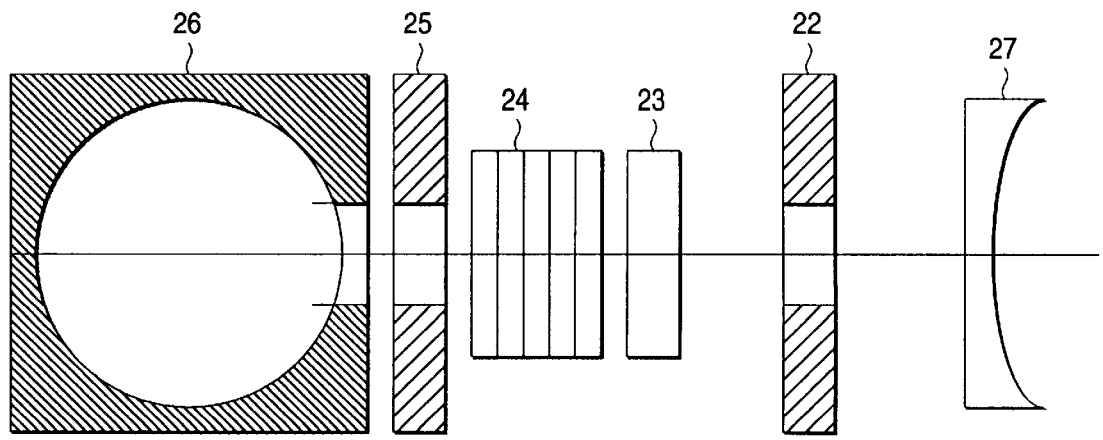
FIG. 6 is a sectional view showing a measuring system for confirming the effects of the invention.

An empirical methodology for proving the validity of the condition satisfying method to satisfy the condition 2) will be described. In a measuring apparatus used, an integral sphere was assembled into a spectro-photometer. A schematic illustration of a key portion of the measuring apparatus is shown in FIG. 6. Light of a single wavelength is emitted from a monochrometer of the spectro-photometer; is projected onto a object; enters an integral sphere 26; is distributed uniformly within the integral sphere 26; and a light intensity within the integrating sphere is measured. The center optical path of the light rays lies on the line passing through the center in the figure An object 24 in the figure corresponds to the living tissue. The object consists of a lamination of milky-white acrylic plates of 1mm thick. An optical attenuation by scattering of the object is nearly equal to that of the living tissue. A scattering plate 23 is located in close proximity to the incident surface of the object. With provision of the scattering plate, scattering light is incident on the object The light emitting surface of the object is brought into close contact with a transmission window 25. With provision of the transmission window, only transmitted light within a predetermined area of the object is allowed to be incident on the integral sphere 26, and measured. A window of the integral sphere 26 is much larger than the transmission window 25 Light emitted from the monochrometer is properly sized by a concave lens 27, and is projected onto an area defined by an incident window 22, located between the concave lens 27 and the scattering plate 23.

Addition of one sheet of acrylic plate increases the thickness of the object by 1 mm. The increment of 1 mm is denoted as ΔD. An optical density ΔA of the thickness increment will be calculated by use of an increment of an optical attenuation of the transmitted light caused by the thickness increment. A ratio of the optical density to the thickness increment is an optical attenuation rate Z; Z=ΔA/ΔD. The attenuation rate Z of the object was measured while varying the wavelength of the monochrometer from 400 nm to 900 nm.

When the object is made of milky-white acrylic, light is not absorbed in a region of those wavelengths. Therefore, the measurement result is a non-absorptive attenuation. When the scattering plate is not used, the attenuation rate varies while ascending to the left when graphed. This arises from the fact that light rays tend to make larger scatter in a region of shorter wavelengths. When the scattering plate is present, the curve becomes flat.

Figure 7:
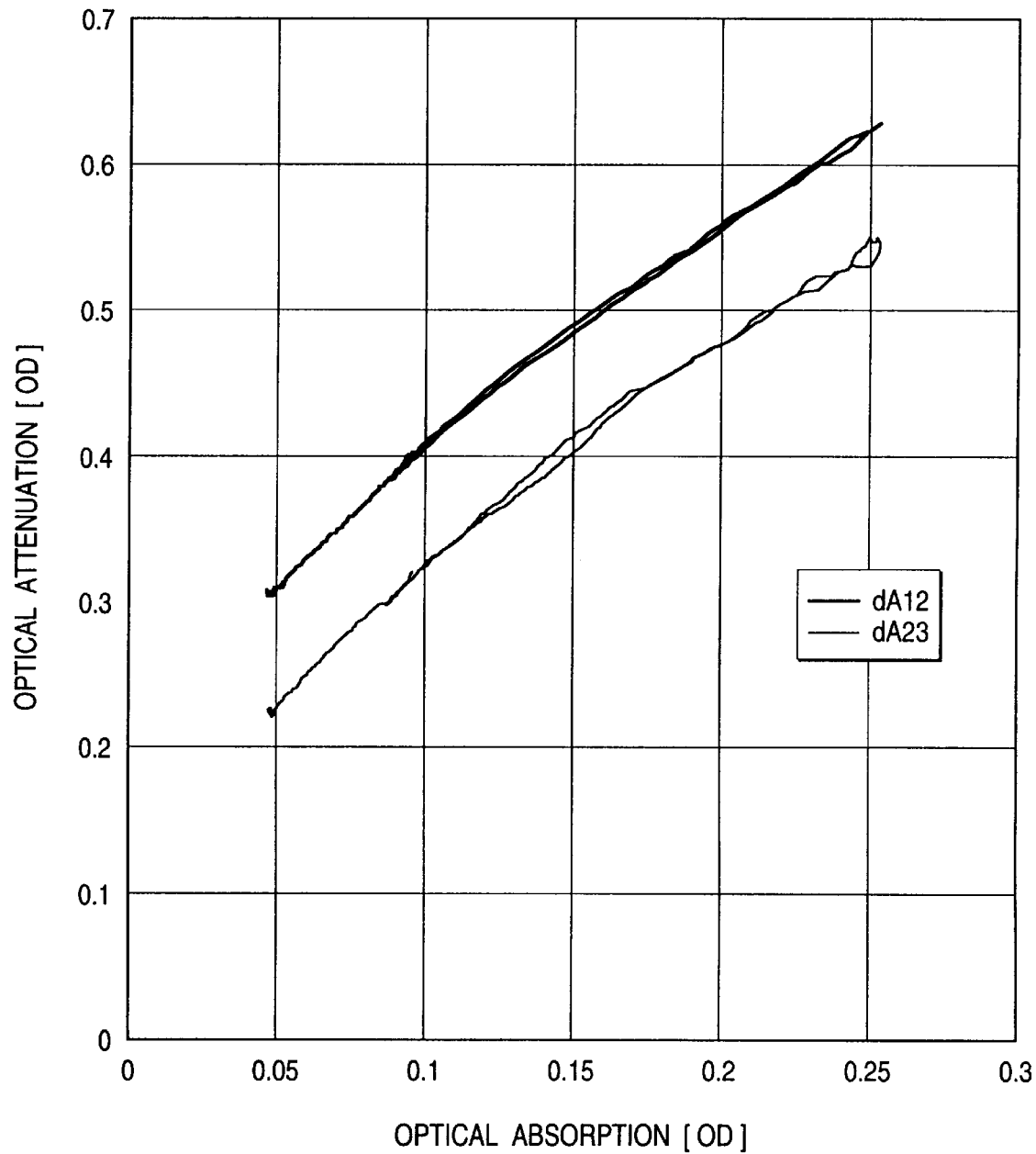
FIG. 7 is a graph showing the results of the measurement by the FIG. 6 system.
Figure 8:
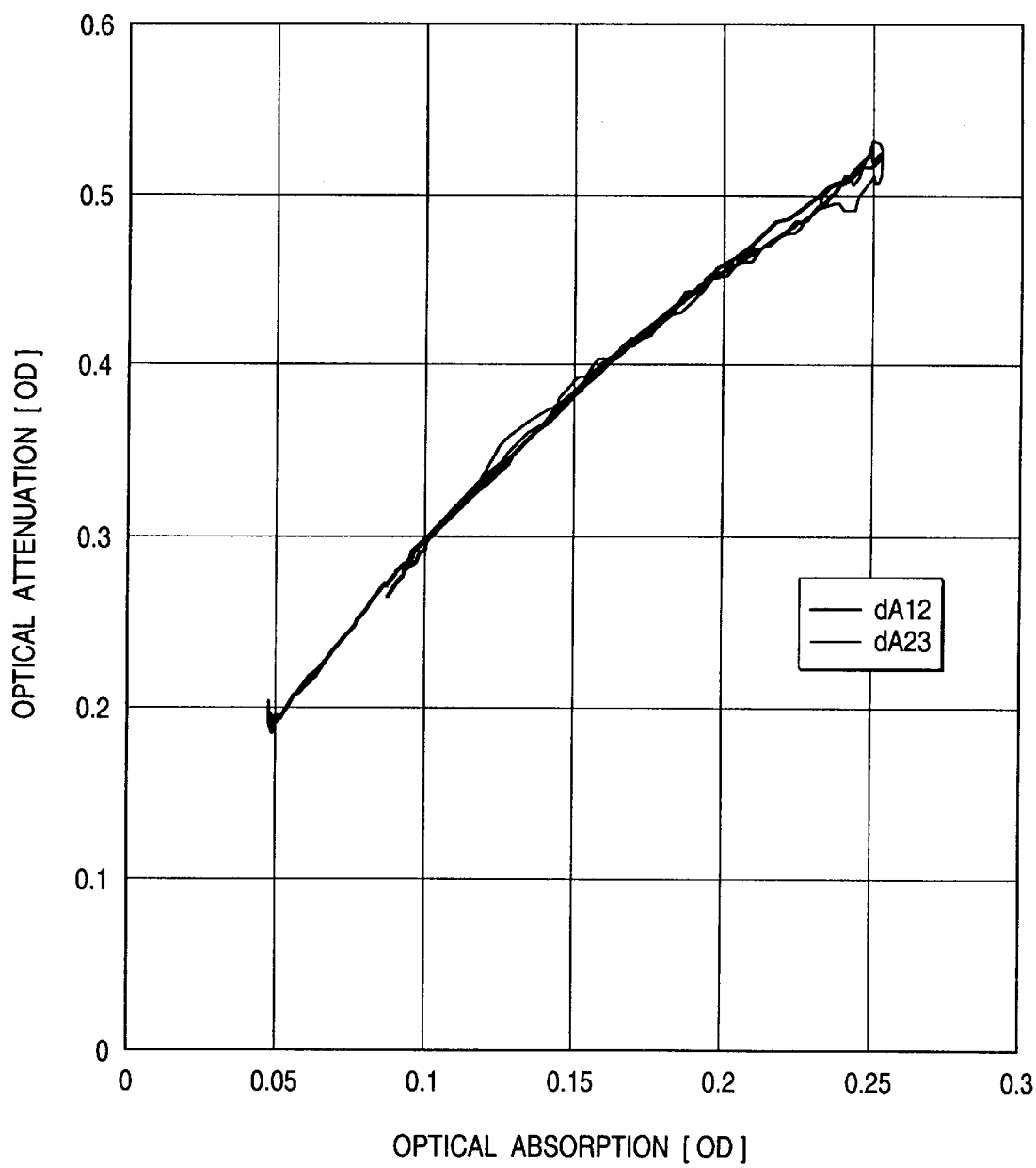
FIG. 8 is a graph showing additional results of the measurement by the FIG. 6 system.
Figure 9:
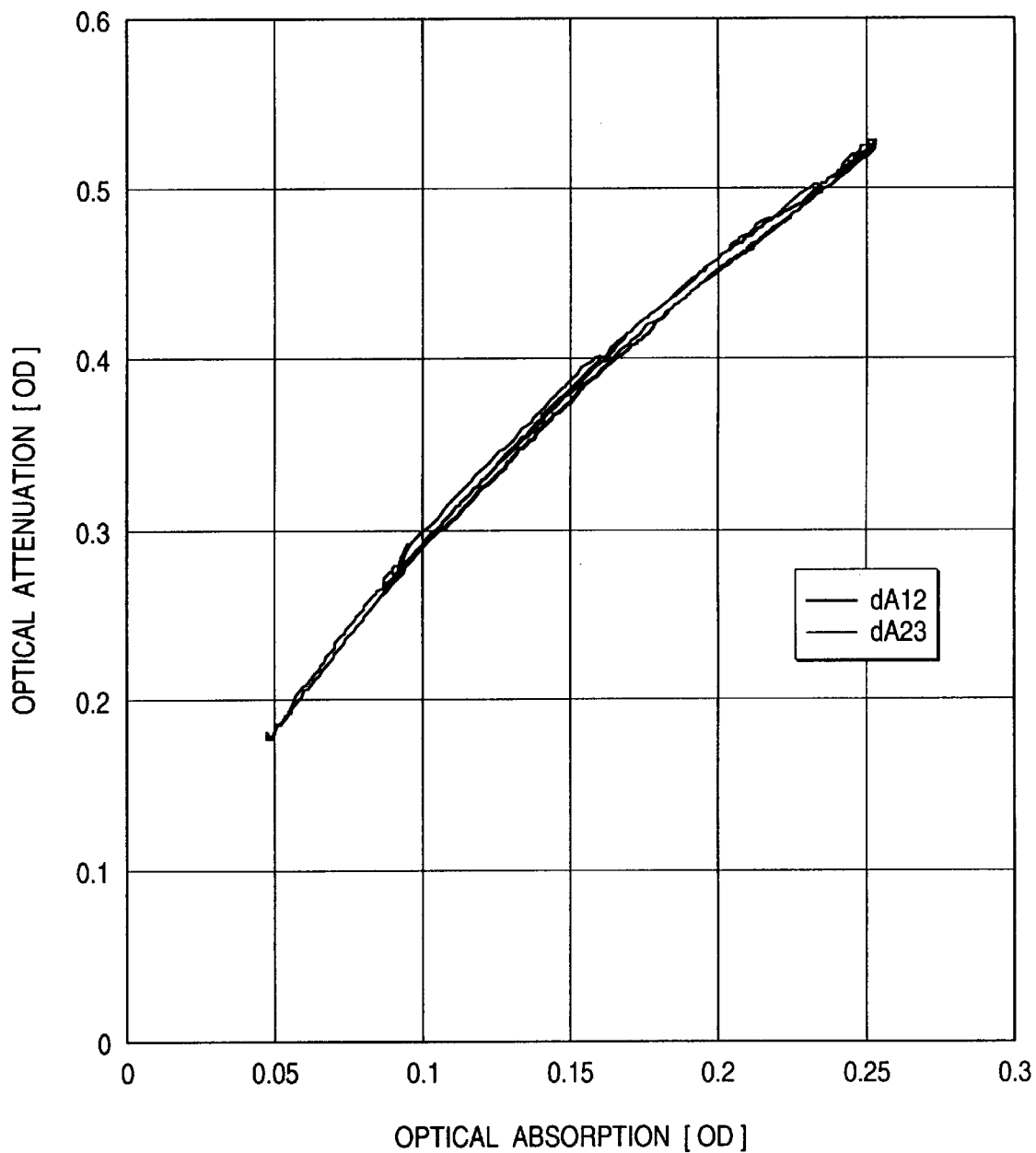
FIG. 9 is a graph showing further results of the measurement by the FIG. 6 system.

When a transparent color film is stuck over a milky-white acrylic plate of 1 mm thick as an object, optical absorption varies with the wavelength. Therefore, a relationship between optical absorption and absorptive attenuation can be obtained by sticking the color film on the acrylic plate. In this case, a white acrylic plate of 1 mm thick was used for the scattering plate, whereby light incident on the object is sufficiently scattered. To obtain the relationship, optical attenuation (=ordinate) vs. optical absorption (=abscissa) relationship may be graphed as shown in FIGS. 7 to 9. In those graphs, ΔA12 and ΔA23 are increments of the optical densities of the object when it is increased in number from one sheet to two sheets, and when it is increased in number from two sheets to three sheets. Some amount of noise caused by the spectroscope is superposed on the measurement result.

To plot curves in FIG. 7, an incident window was 4 mm in diameter and a transmission window was 6 mm in diameter (area ratio≈2.2). As seen from the graph, a variation curve of the extinction with respect to the absorption in the case of ΔA12 resembles that in the case of ΔA23. The rise of the curve in the case of ΔA23 is somewhat sharper than the curve in the case of ΔA12, and a curvature of the former curve is somewhat larger than the latter curve. To plot curves in FIG. 8, an incident window was 12 mm in diameter and a transmission window was 6mm in diameter (area ratio=4). The measuring values in the case of ΔA12 are also equal to those in the case of ΔA23 To plot curves in FIG. 9, an incident window was 6 mm in diameter and a transmission window was 12 mm in diameter (area ratio=4). The measuring values in the case of ΔA12 are equal to those in the case of ΔA23.

From the foregoing description, it is seen that to satisfy Schuster'theory in the living tissue measurement,the irradiation area on the living tissue must be selected to be at least two times as large as the light receiving area or the light receiving area on the living tissue must be selected to be at least two times as large as the irradiation area on the same.

First Embodiment

A pulse oximeter which is a first embodiment of the present invention will be described. The principles of the first embodiment will first be described. Schuster's theory mathematically describes an optical density change $\Delta Ab$ caused by a blood-thickness change $\Delta Db$ by the following expression. For details of the theory, reference is made to "Theoretical and Empirical Study on Extinction in Blood" written by Takuo Aoyagi, 30(1), pp1 to 7, 1992 in "Medical Electronics and Biomedical Engineering".

$$\Delta Ab = \{Eh(Eh+F)\}^{1/2} * Hb\Delta Db \quad (1)$$

$$Eh = SEo + (1-S)Er \quad (2)$$

In the above expressions, Eo is an absorption coefficient of oxyhemoglobin; Hb is a hemoglobin concentration; $\Delta Db$ is a blood-thickness change; F is a blood scattering coefficient; S is an oxygen saturation $SaO_2$ in arterial blood; and Er is an absorption coefficient of reduced hemoglobin.

Tissue exclusive of the blood will be referred to as a pure tissue. Light absorption by water, which is one of the light absorbing materials in the pure tissue, can be considered to be sufficiently small if the wavelength of light is appropriately selected. Light absorption of other light absorbing materials than the water can be considered to be sufficiently small compared with that of blood Therefore, optical absorption by the pure tissue can be approximated to zero. A change $\Delta At$ of an optical density caused by a tissue-thickness change $\Delta Dt$ is mathematically expressed by $$\Delta At = Zt * \Delta Dt \quad (3)$$

where Zt=optical density of the tissue.

An arterial blood in the living tissue is pulsating, and hence, the substantial thickness of blood is also periodically varying. Accordingly, the substantial thickness of the pure tissue is also periodically varying. Inmost cases, a direction of this variation is opposite to that of the variation of the blood. Therefore, a change $\Delta A$ of an extinction coefficient of the whole tissue including blood is equal to a difference between a change $\Delta Ab$ of the optical density of the blood and a change $\Delta At$ of the optical density of living tissue, and mathematically expressed by $$\Delta A = \Delta Ab - \Delta At = \{Eh(Eh+F)\}^{1/2} * Hb\Delta Db - Zt * \Delta Dt \quad (4)$$

Let us calculate a ratio of changes of optical density of a living tissue at three wavelengths $\lambda 1$, $\lambda 2$ and $\lambda 3$.

An optical density change ratio at the wavelengths $\lambda 1$ and $\lambda 2$ is given by $$\Phi 12 = \Delta A1/\Delta A2 = [\{Eh1(Eh1+F)\}^{1/2} * Hb\Delta Db - Zt1 * \Delta Dt]/[\{Eh2(Eh2+F)\}^{1/2} * Hb\Delta Db - Zt2 * \Delta Dt] \quad (5)$$

Defines as follows:

$$Ex1 = (Zt1 * \Delta Dt)/Hb * \Delta Db) \quad (6)$$

$$Ex2 = (Zt2 * \Delta Dt)/Hb * \Delta Db) \quad (7)$$

Then, $$\Phi 12 = \Delta A1/\Delta A2 = [\{Eh1(Eh1+F)\}^{1/2} - Ex1]/[\{Eh2(Eh2+F)\}^{1/2} - Ex2] \quad (8)$$

Similarly, an optical density change ratio at the wavelengths $\lambda 2$ and $\lambda 3$ is given by $$\Phi 32 = \Delta A2/\Delta A3 = [\{Eh3(Eh3+F)\}^{1/2} - Ex3]/[\{Eh2(Eh2+F)\}^{1/2} - Ex2] \quad (9)$$

In the above equations, Zt1, Zt2 and Zt3 are non-absorptive attenuation. In the measuring system of the present invention, the non-absorptive attenuation is not dependent on the wavelength. In this sense, the non-absorption optical density may be denoted as Ex. Accordingly, the equations (8) and (9) can be rewritten into $$\Phi 12 = \Delta A1/\Delta A2 = [\{Eh1(Eh1+F)\}^{1/2} - Ex]/[\{Eh2(Eh2+F)\}^{1/2} - Ex] \quad (10)$$

$$\Phi 32 = \Delta A3/\Delta A2 = [\{Eh3(Eh3+F)\}^{1/2} - Ex]/[\{Eh2(Eh2+F)\}^{1/2} - Ex] \quad (11)$$

where $$Ehi = SEoi + (1-S)Eri (i=1, 2, 3, \text{ corresponding to } \lambda 1, \lambda 2 \text{ and } \lambda 3) \quad (12)$$

In these simultaneous equations, optical density changes $\Delta A1$, $\Delta A2$ and $\Delta A3$ may be measured, and therefore $\Phi 12$ and $\Phi 13$ can be calculated. Eo1, Eri and F are known. Therefore, unknown values are only S and Ex. Solution of the simultaneous equations will produce S and Ex.

An overall arrangement of the pulse oximeter constructed on the basis of the above-mentioned principles of the present invention is shown in FIG. 1. The pulse oximeter generally includes a probe 1 and a body 2.

Figure 2:
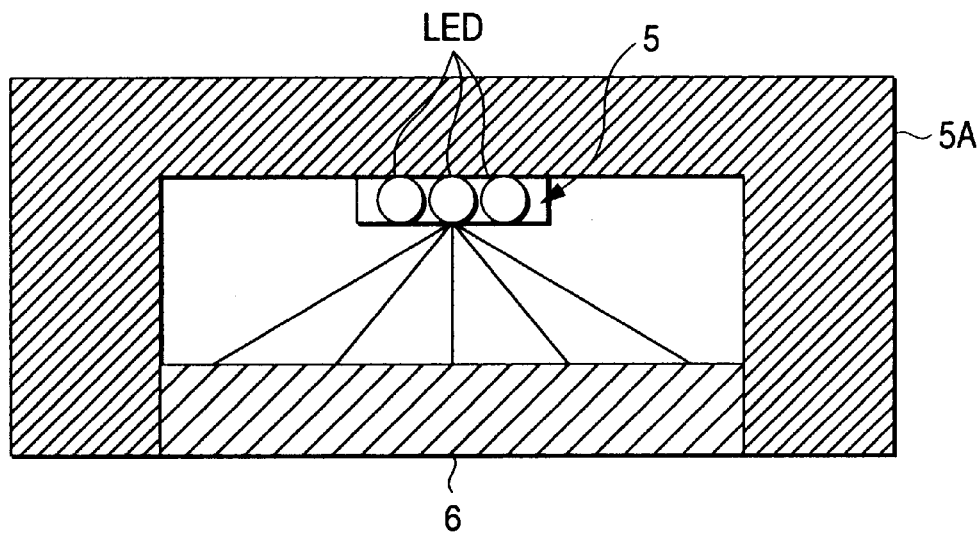
FIG. 2 is a sectional view showing a structure of a light irradiating means shown in FIG. 1.

The probe 1 includes light irradiating section 3 for generating scattering light, and light receiving section 4. The irradiating section 3 is constructed with a light source 5 as an LED, for example, and a scattering plate 6 for receiving light from the light source 5 and scattering the light. A specific construction of the irradiating section 3 is shown in FIG. 2. As shown, the light source 5 consists of three LEDs. Those LEDs are attached to the inner wall of a housing 5A, which is confronted with an opening of the same. The scattering plate 6 is fit into the opening. The three LEDs emit light of different wavelengths. The scattering plate 6 is preferably a white acrylic plate of approximately 0.5 mm thick. As shown in FIG. 1, the irradiating section 3 and the light receiving section 4 are disposed to face the each other. Namely, when attaching the probe to the living tissue, the living tissue is interposed between the irradiating section 3 and the light receiving section 4 which are confronted with each other. The incident surface of the light irradiating section is much larger than the light receiving surface. A ratio of those surfaces is at least 2:1. The probe 1 is provided with holding means (not shown), which is used for tightly attaching the irradiating section 3 and the light receiving section 4 to a living tissue (e.g., the earlobe or finger of a patient). The light receiving section 4 includes a photodiode in this embodiment, and receives transmitted light from the living tissue and converts it into a corresponding electrical signal.

The machine body 2 includes an analog processor 7, an A/D converter 8, a light-source driver 9 and a digital processor 10. The analog processor 7 removes noise and amplifies the output signal of the light receiving section 4. The A/D converter 8 converts an output signal of the analog processor 7 into a corresponding digital signal. The light-source driver 9 drives the LEDs of the light source 5. The digital processor 10 consists of a computer, and more precisely a CPU (central processing unit) for arithmetic and control operations, a memory for storing a process program and necessary data, an input/output interface for providing a signal and data path to and from an external device. The digital processor 10 may functionally be expressed as shown in FIG. 1. As shown, it includes a Φ calculator portion 11 for calculating Φ using data received from the A/D converter 8, a converter portion 12 for calculating an arterial oxygen saturation $SaO_2$ by use of the Φ calculated by the Φ calculator portion 11, and a controller portion 13 for controlling the operations of the overall pulse oximeter. The value of the thus obtained oxygen saturation $Sao_2$ is usually denoted as $SpO_2$.

Figure 3:
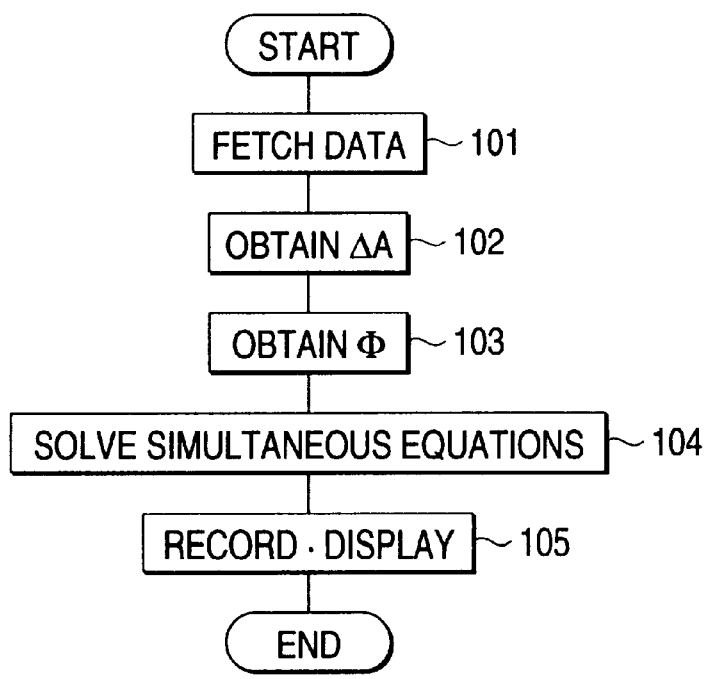
FIG. 3 is a flow chart showing an operation of the pulse oximeter.

An operation of the pulse oximeter thus constructed will be described. FIG. 3 is a flow chart of a process carried out by the digital processor 10. Now, description will be given with reference to the flow chart.

To start with, the irradiating section 3 irradiates a living tissue with scattering light. The digital processor 10 starts to retrieve or fetch data from the A/D converter 8 (step 101). Data fetched here is data of light intensity at three waves, λ1, λ2 and λ3, transmitted through the living tissue.

A change ΔA of an optical density of each light of three waves is calculated (step 102). A transmitted light emanating from the living tissue is pulsating. Changes ΔA1, ΔA2, and ΔA3 of optical densities of the light of three wavelengths are given by $$\Delta A1 = \text{Log}[L1/(L1-\Delta L1)] \quad (13)$$

$$\Delta A2 = \text{Log}[L2/(L2-\Delta L2)] \quad (14)$$

$$\Delta A3 = \text{Log}[L3/(L3-\Delta L3)] \quad (15)$$

Then, the Φ is calculated (step 103). Φ12 and Φ13 are calculated by substituting ΔA1, ΔA2, and ΔA3 calculated in the step 102 into the following equations.

$$\Phi 12 = \Delta A1/\Delta A2 \quad (16)$$

$$\Phi 32 = \Delta A3/\Delta A2 \quad (17)$$

Unknown values S and Ex are obtained by substituting the Φ into the equations (10) and (11) (step 104).

The value of S obtained is stored as an oxygen saturation $SpO_2$ into the related memory and output to a related device (step 105).

Figure 11:
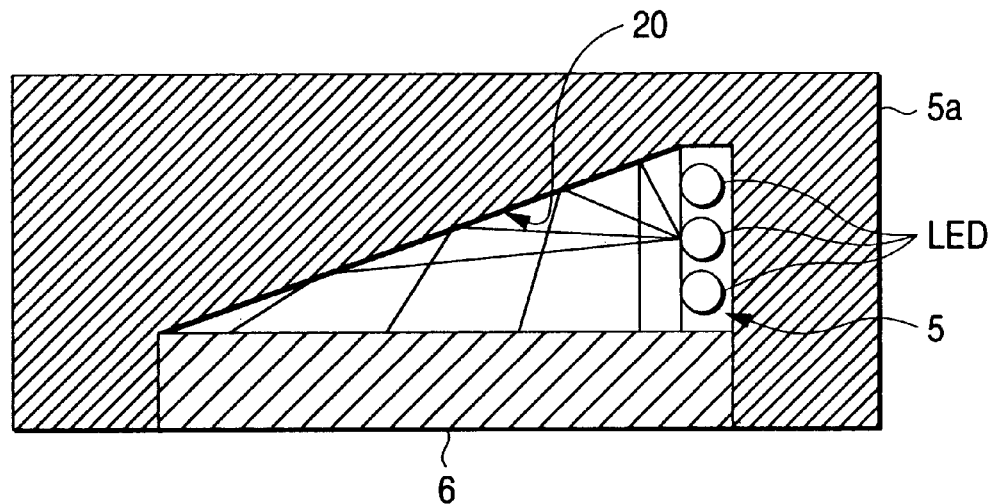
FIG. 11 is a sectional view showing a structure of another light irradiating means.
Figure 12:
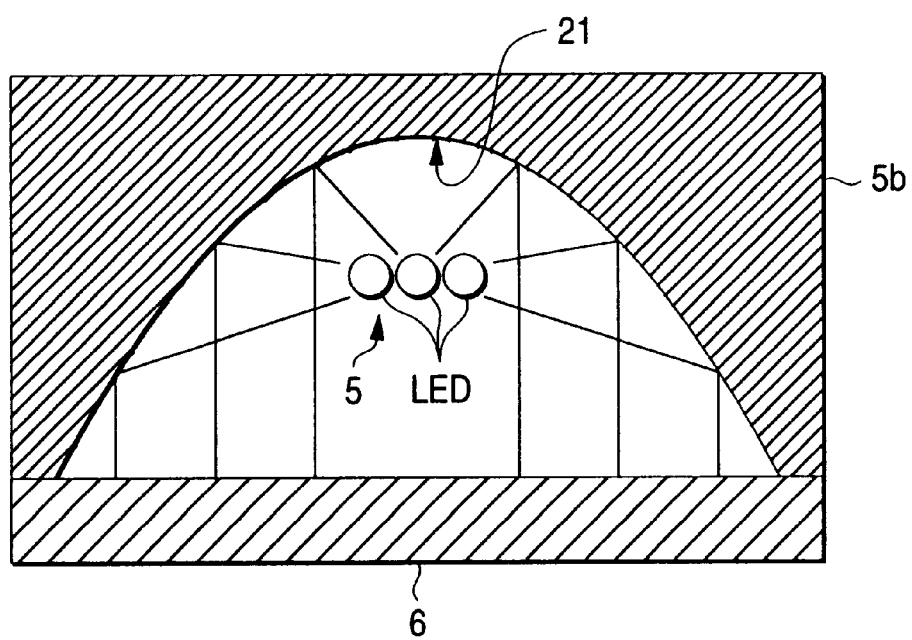
FIG. 12 is a sectional view showing a structure of yet another light irradiating means.

FIG. 11 is a diagram showing another irradiating means. In the embodiment, the inner wall of a housing 5a is used as a reflecting surface 20. It uniformly reflects light rays from a light source (LEDs) 5 to a scattering plate 6. FIG. 12 is a diagram showing yet another irradiating means. In this irradiating means, the inner curved surface of a housing 5b is used as a reflecting surface 21. It uniformly reflects light rays from a light source (LEDs) 5 to a scattering plate 6. The irradiating means is thus constructed in order to irradiate a broad area on the living tissue with a sufficient amount of scattering light.

In the pulse oximeter, the irradiating means and the light receiving means are oppositely disposed so that the light receiving means receives light transmitted through the living tissue. The construction of the probe may be modified so that the light receiving means receives reflecting light.

Figure 4:
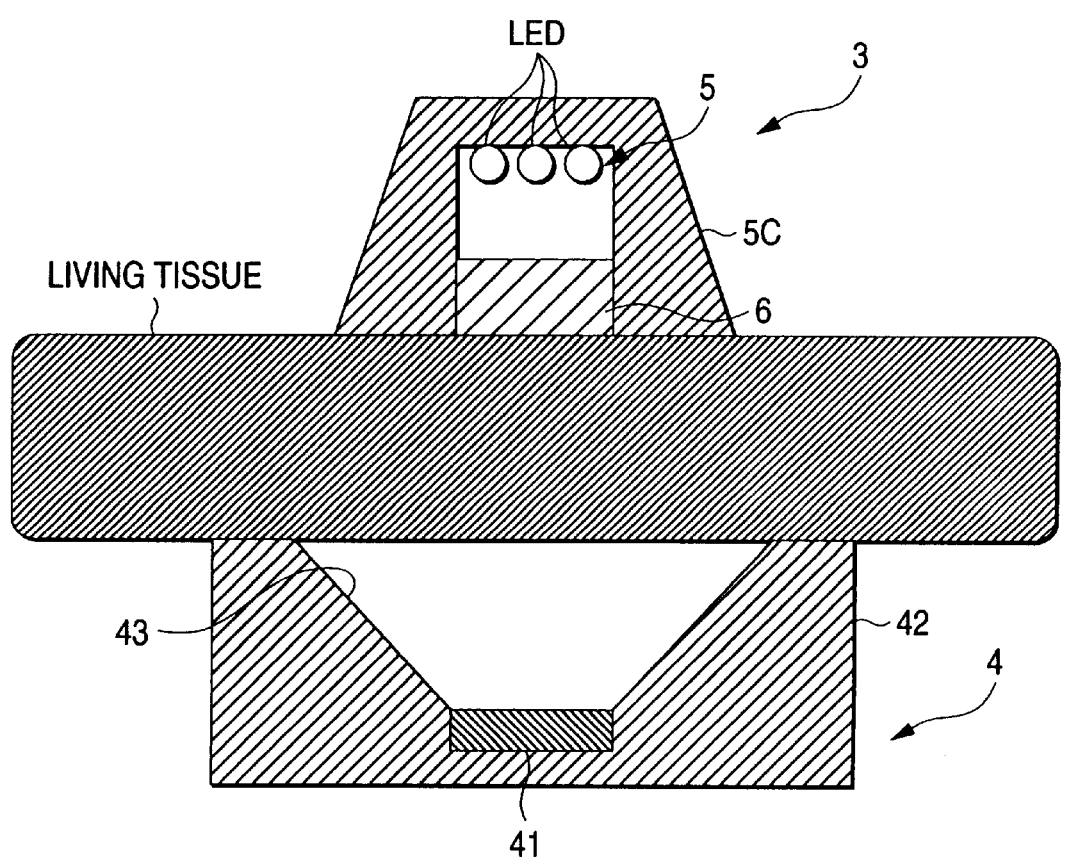
FIG. 4 is a sectional view showing another probe.

Sufficiently large incident area compared with receiving area was used in the above-mentioned embodiment. On the contrary, the probe may be constructed such that the receiving area is selected to be much larger than the incident area. An example of this construction is shown in FIG. 4. As shown, a scattering plate 6 is fit into an opening of a housing 5c of the irradiating section 3. Light emitted from the light source 5 of LEDs is scattered by the scattering plate 6, and then projected into a living tissue. The inner surface of the housing is coated with white coating to form a light scattering surface. Light receiving section 4 includes a photo-diode 41 and a housing 42 for holding the photo diode. A concavity 43 of the housing 42 is shaped such that the diameter of the concavity increases from the bottom to the top or opening. The photodiode 41 is placed at the bottom of the concavity 43. The inner surface of the concavity 43 is also coated with white coating to form a light scattering surface. In the probe, the light receiving surface is sufficiently larger than the incident surface. A ratio of their area sizes is at least 2:1. This probe produces useful effects comparable with the probe where the incident surface is much larger than the light receiving surface.

In the pulse oximeter described above, two unknown values S and Ex are obtained by use of light of three wavelengths.

Second Embodiment

A second embodiment of the present invention will be described. The embodiment is a dye dilution curve measuring device. A construction similar to that mentioned above is capable of profiling a dye dilution curve. In this case, dye is added to the in-blood light absorbing materials. Accordingly, unknown factors are oxygen saturation S, in-blood dye concentration Cd, and tissue terms Ex. Therefore, three equations are used for simultaneous equations. The irradiating means is constructed so as to emit light of four wavelengths toward a living tissue. The device measures three change ratios Φ, i.e., Φ12, Φ32, Φ42, and produces S, Cd and Ex by substituting those Φ12, Φ32 and Φ42 into the following simultaneous equations.

$$\Phi 12 = [\{Eh1+Ed1Cd/Hb\}(Eh1+Ed1Cd/Hb+F)\}^{1/2}-Ex]/[\{Eh2+Ed2Cd/Hb\}(Eh2+Ed2Cd/Hb+F)\}^{1/2}-Ex] \quad (18)$$

$$\Phi 32 = [\{Eh3+Ed3Cd/Hb\}(Eh3+Ed3Cd/Hb+F)\}^{1/2}-Ex]/[\{Eh2+Ed2Cd/Hb\}(Eh2+Ed2Cd/Hb+F)\}^{1/2}-Ex] \quad (19)$$

$$\Phi 42 = [\{Eh4+Ed4Cd/Hb\}(Eh4+Ed4Cd/Hb+F)\}^{1/2}-Ex]/[\{Eh2+Ed2Cd/Hb\}(Eh2+Ed2Cd/Hb+F)\}^{1/2}-Ex] \quad (20)$$

In the above equations, Ed is an absorption coefficient of dye; Cd is a dye concentration in blood; and Hb is a hemoglobin concentration. A dye dilution curve can be obtained by successively measuring the in-blood dye concentration Cd. Other light absorbing materials, e.g., COHb, may be measured in similar ways.

In the embodiments thus far described, pulsations of light transmitted through the living tissue are used for measuring the concentrations of the in-blood light absorbing materials. It is clear that the present invention may be applied to a near-infrared spectrometry (NIRS) in which pulsations of the transmitted light are not used.

The present invention has the following advantages when it is applied to the measurement of the concentrations of light absorbing materials in a living tissue.

1) The optical path is not dependent on this wavelength.
2) Non-absorptive attenuation is not dependent on the wavelength.
3) The optical absorption/optical attenuation is expressed by a simple formula.

Therefore, an accurate measurement of the concentrations of light absorbing materials in a living tissue is possible. Particularly, it is easy and accurate to simultaneously measure multiple materials by use of multiple wavelengths.

It will be apparent to those skilled in the art that various modifications and variations can be made to the apparatus for determining concentrations of light-absorbing materials in living tissue according to the present invention without departing from the spirit or scope of the invention. Thus, it is intended that the present invention covers the modifications and variations of the invention provided they come within the scope of the appended claims and their equivalents.

What is claimed is:

1. An apparatus for measuring a ratio of concentration of light absorbing materials in a living tissue, comprising:
   irradiating means for irradiating a living tissue with scattered light of different wavelengths;
   light receiving means for receiving either light transmitted through or light reflected from said living issue and for converting said light into corresponding electric signals; and
   concentration-ratio processing means for calculating ratios of concentrations of light absorbing materials in accordance with said corresponding electric signals on the assumption that non-absorptive attenuation is equal independently of the wavelengths of light,
   wherein said concentration-ratio processing means calculates changes of optical densities of the living tissue by use of pulsations of intensities of transmitted light, and calculates a ratio of concentrations of light absorbing materials by use of said calculated changes of the optical densities.

2. An apparatus as claimed in claim 1, wherein said irradiating means includes a scattering plate and light source for irradiating light to said living tissue through said scattering plate.

3. An apparatus for measuring a ratio of concentration of light absorbing materials in a living tissue, comprising:
   irradiating means for irradiating a living tissue with scattered light of different wavelengths;
   light receiving means for receiving either light transmitted through or light reflected from said living issue and for converting said light into corresponding electric signals; and
   concentration-ratio processing means for calculating ratios of concentrations of light absorbing materials in accordance with said corresponding electric signals on the assumption that non-absorptive attenuation is equal independently of the wavelengths of light,
   wherein said concentration-ratio processing means calculates a ratio of concentrations of light absorbing materials using a theoretical formula where values representing tissue exclusive of the blood at respective wavelengths are equal, and
   wherein said concentration-ratio processing means calculates changes of optical densities of the living tissue by use of pulsations of intensities of transmitted light, and calculates a ratio of concentrations of light absorbing materials by use of said calculated changes of the optical densities.

4. An apparatus as claimed in claim 3, wherein said irradiating means includes a scattering plate and light source for irradiating light to said living tissue through said scattering plate.

5. An apparatus for measuring a ratio of concentration of light absorbing materials in a living tissue, comprising:
   irradiating means for irradiating a living tissue with scattered light of different wavelengths;
   light receiving means for receiving either light transmitted through or light reflected from said living issue and for converting said light into corresponding electric signals; and
   concentration-ratio processing means for calculating ratios of concentrations of light absorbing materials in accordance with said corresponding electric signals on the assumption that non-absorptive attenuation is equal independently of the wavelengths of light,
   wherein said concentration-ratio processing means includes:
      optical density-change calculating means for calculating optical density changes $\Delta A1$ to $\Delta A2, \ldots \Delta An$ of n number of wavelengths from the pulsations of either light transmitted through or light reflected from said living tissue;
      optical density change-ratio calculating means for calculating a ratio $\Phi ij$ of two optical density changes ($\Delta Ai$, $\Delta Aj$), which are preselected from among the n number of optical density changes $\Delta A1$ to $\Delta An$ calculated by said optical density-change calculating means;
      processing means for calculating at least one of an arterial oxygen saturation and a ratio of concentrations of another in-blood light absorbing material by use of n−1 number of $\Phi ij$ obtained by said optical density change-ratio calculating means and an n−1 number of simultaneous equations constructed such that values representing tissue exclusive of the blood at respective wavelengths are equal.

6. An apparatus for measuring a ratio of concentration of light absorbing materials in a living tissue, comprising:
   irradiating means for irradiating a living tissue with scattered light of different wavelengths;
   light receiving means for receiving either light transmitted through or light reflected from said living issue and for converting said light into corresponding electric signals; and
   concentration-ratio processing means for calculating ratios of concentrations of light absorbing materials in accordance with said corresponding electric signals on the assumption that non-absorptive attenuation is equal independently of the wavelengths of light,
   wherein said concentration-ratio processing means calculates a ratio of concentrations of light absorbing materials using a theoretical formula where values representing tissue exclusive of the blood at respective wavelengths are equal, and
   wherein said concentration-ratio processing means includes:
      optical density-change calculating means for calculating optical density changes $\Delta A1$ to $\Delta A2, \ldots \Delta An$ of n number of wavelengths from the pulsations of either light transmitted through or light reflected from said living tissue;
      optical density change-ratio calculating means for calculating a ratio $\Phi ij$ of two optical density changes ($\Delta Ai$, $\Delta Aj$), which are preselected from among the n number of optical density changes $\Delta A1$ to $\Delta An$ calculated by said optical density change calculating means;
      processing means for calculating at least one of an arterial oxygen saturation and a ratio of concentrations of another in-blood light absorbing material by use of n−1 number of $\Phi ij$ obtained by said optical density change-ratio calculating means and an n−1 number of simultaneous equations constructed such that the values of tissue exclusive of the blood at respective wavelengths are equal.

7. An apparatus for measuring a ratio of concentration of light absorbing materials in a living tissue, comprising:
   irradiating means for irradiating a living tissue with scattered light of different wavelengths;
   light receiving means for receiving either light transmitted through or light reflected from said living issue and for converting said light into corresponding electric signals; and concentration-ratio processing means for calculating ratios of concentrations of light absorbing materials in accordance with said corresponding electric signals on the assumption that non-absorptive attenuation is equal independently of the wavelengths of light, wherein said concentration-ratio processing means calculates changes of optical densities of the living tissue by use of pulsations of intensities of transmitted light, and calculates a ratio of concentrations of light absorbing materials by use of said calculated changes of the optical densities, and wherein said concentration-ratio processing means includes:

optical density-change calculating means for calculating optical density changes $\Delta A1$ to $\Delta A2, \ldots \Delta An$ of n number of wavelengths from the pulsations of either light transmitted through or light reflected from said living tissue;

optical density change-ratio calculating means for calculating a ratio $\Phi ij$ of two density changes ($\Delta Ai$, $\Delta Aj$), which are preselected from among the n number of optical density changes $\Delta A1$ to $\Delta An$ calculated by said optical density-change calculating means;

processing means for calculating at least one of an arterial oxygen saturation and a ratio of concentrations of another in-blood light absorbing material by use of n−1 number of $\Phi ij$ obtained by said optical density change-ratio calculating means and an n−1 number of simultaneous equations constructed such that values representing tissue exclusive of the blood at respective wavelengths are equal.

8. An apparatus for measuring a ratio of concentration of light absorbing materials in a living tissue, comprising:

irradiating means for irradiating a living tissue with scattered light of different wavelengths;

light receiving means for receiving either light transmitted through or light reflected from said living issue and for converting said light into corresponding electric signals; and concentration-ratio processing means for calculating ratios of concentrations of light absorbing materials in accordance with said corresponding electric signals on the assumption that non-absorptive attenuation is equal independently of the wavelengths of light, wherein an area for receiving either light transmitted through said living tissue or light reflected from said living tissue is sufficiently larger or smaller than an irradiation area on said living tissue, and wherein a ratio of said irradiating area on said living tissue to an effective area of said light receiving area on said living tissue is 1:2 or more or 2 or more 0:1.

* * * * *